(12) United States Patent
Berdut-Teruel

(10) Patent No.: US 7,955,251 B2
(45) Date of Patent: Jun. 7, 2011

(54) MAGNETIC THERAPEUTICALL MALE DEVICE

(76) Inventor: Elberto Berdut-Teruel, Carolina, PR (US)

( * ) Notice: Subject to any disclaimer, the term of this patent is extended or adjusted under 35 U.S.C. 154(b) by 380 days.

(21) Appl. No.: 12/247,252

(22) Filed: Oct. 8, 2008

(65) Prior Publication Data

US 2010/0087704 A1    Apr. 8, 2010

(51) Int. Cl.
*A61F 5/00*    (2006.01)
(52) U.S. Cl. ............................................. 600/38; 600/15
(58) Field of Classification Search ................ 600/9–15, 600/38–41
See application file for complete search history.

(56) References Cited

U.S. PATENT DOCUMENTS

| | | | | |
|---|---|---|---|---|
| 435,343 | A | * | 8/1890 | Brown ........................... 600/13 |
| 435,376 | A | * | 8/1890 | Brown ........................... 600/13 |
| 1,001,236 | A | * | 8/1911 | Bachelet ........................ 600/13 |
| 3,658,051 | A | * | 4/1972 | MacLean ....................... 600/14 |
| 2007/0038015 | A1 | * | 2/2007 | Quail ............................... 600/9 |
| 2007/0083237 | A1 | * | 4/2007 | Teruel .............................. 607/1 |

OTHER PUBLICATIONS

New Riverside University Dictionary, 1984, p. 875.*

* cited by examiner

*Primary Examiner* — John P Lacyk
(74) *Attorney, Agent, or Firm* — Luis Figarella

(57) ABSTRACT

The invention refers to a therapeutic device used on or in interaction with a penile organ of a human, and more particularly to a C-shaped male genital device made of durable resilient material, easy to attach and clean, which promotes an increase in the penis size when erected, enhancing the user's sexual experience and providing a therapeutic magnetic field.

2 Claims, 3 Drawing Sheets

MAGNETIC THERAPEUTICALL MALE DEVICE

STATEMENT REGARDING FEDERALLY SPONSORED RESEARCH AND DEVELOPMENT

N/A

RELATED APPLICATIONS

N/A

BACKGROUND OF THE INVENTION

1. Field of the Invention

The invention relates to a male genital device made of a durable resilient material, easy to attach and clean, which goes attached around the penile organ of a human.

2. Discussion of the Background

The ability to produce and maintain a complete erection has been a problem in men of all ages. An erection is produced when certain tissue becomes widely dilated and enlarged with blood. The corpus cavernosum penis is one of a pair of sponge-like regions of erectile tissue which contain most of the blood in the male penis during erection. The two corpora cavernosa are located along the penis body, basically from the pubic bones to the head of the penis. Therefore a good flow of blood in this area represents an enhanced erection.

Several tests have proven that when applying magnets to body's areas magnetic energy penetrates the users body and creates a magnetic field that energizes, speeds up circulation and helps oxygenate the blood. Therefore magnets are used to increase the blood flow and ease the pain while performing a natural healing function.

Magnetic therapy has caused development of products using permanent magnets. Some of these products are provided to interact with the male organ as rings. Most of them comprise a circular structure made of rubber wherein magnetic pieces are provided around the inner surface of the product. However, this type of structure tends to be difficult to adjust, covers a big area and also the material tends to carry odors from the contact with several human fluids. Also most of these devices are likely to be damaged at the cleaning process because of the material used.

SUMMARY OF THE INVENTION

The present invention overcomes the disadvantages of the Prior Art and provides a male genital device comprising a main curved body, easy to attach, made of a durable, flexible and stretchable material, and at least two magnetic components attached to the distal ends of said main body.

Another object of the invention is to provide a male genital device easy to clean in order to avoid sanitization without losing flexibility; and carrying odors.

Several minerals, such as iron, travel in the blood. The components' magnetism affects the iron in the blood, increasing the electrical current that travels through. A magnetic field can contribute in the generation of more blood cells and improve the oxygen-carrying capacity, increasing blood circulation, cleansing the impurities contained in the blood. All these events contribute that vasocongestion in this area taking place, making it possible to have a better erection of the penile organ. Therefore another object is to provide a main body having a main curved body positioning the magnetic components in close contact with the corpus cavernosum region.

The invention itself, both as to its configuration and its mode of operation will be best understood, and additional objects and advantages thereof will become apparent, by the following detailed description of a first embodiment taken in conjunction with the accompanying drawings.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying drawings which are incorporated herein constitute part of the specifications and illustrate the invention.

DETAILED DESCRIPTION

Figure 1A:
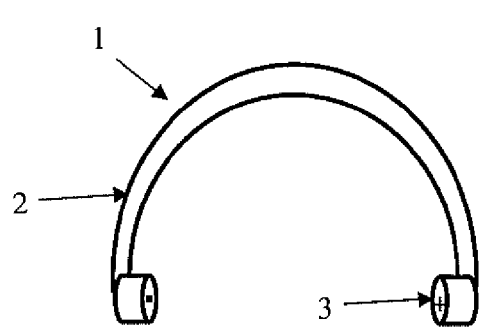
FIG. 1a shows the male genital device.
Figure 1B:
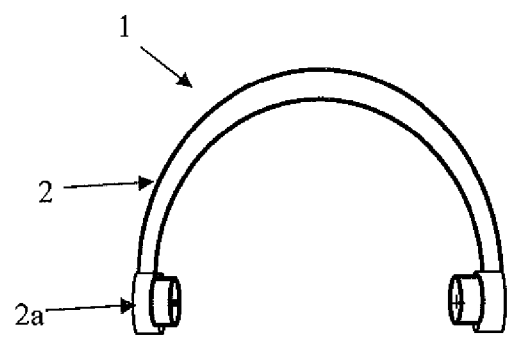
FIG. 1b shows the male genital device with magnetic holders.

FIG. 1a-1b, illustrates the therapeutic device 1 comprising a main curved body 2 and at least two magnetic components 3. The main curved body is made of a flexible band of durable resilient material having magnetic properties and antibacterial properties. The main curved body is substantially a c-shape for the main body 2. The shape provides the advantages of offering a therapeutic device 1 easy to remove and attach compared to a ring-shape which needs to roll all over the penis to be attached and used. The therapeutic device 1, and more particular the main body 2 can be adjusted tightly to the penis in such way that helps maintain the erection after achieved. Different materials can be used, however using magnetic material having antibacterial properties, such as a silver alloy or stainless steel, increases the interaction of the male organ with the magnetic field while providing antibacterial protection.

The therapeutic device 1 has at least two magnetic components, made of magnetic or ferromagnetic material, such as rare-earth magnets, attached to the distal ends of the main body 2. The magnetic component can be attached to the distal ends by different means such as adhesive and others. FIG. 1b shows the use of magnetic holder 2a in order to hold the magnet in position at the distal end. The magnetic holders 2a can be integrally made with the main body 2. The material used for said holders 2a can be different from the one used for the main body 2. For example, the main body 2 can be made of a non-magnetic material to reduce the interaction of the magnetic field with the male organ while the magnetic holder 2a is made of magnetic material in order to easily attach the magnetic components 3 to the main body 2.

Figure 1C:
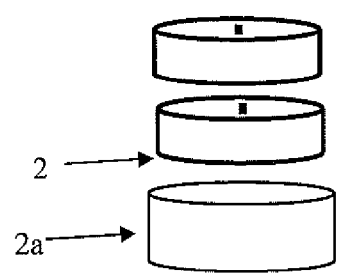
FIG. 1c shows the assembly of multiple magnets at the magnetic holder.

The magnetic field's magnitude provided by the device 1 is controlled by the magnet 3. As illustrated in FIG. 1c in order to increase the magnetic field magnitude each magnetic component comprises multiple magnets 3. Also a combination of magnets with different magnetic properties can be used. The device's 1 thickness, flexibility and dimensions of the components may vary, however in the instant case the material selected to be used was stainless steel with antibacterial properties which is easy to clean in order to afford sanitization without losing flexibility; and carrying odors.

Figure 2:
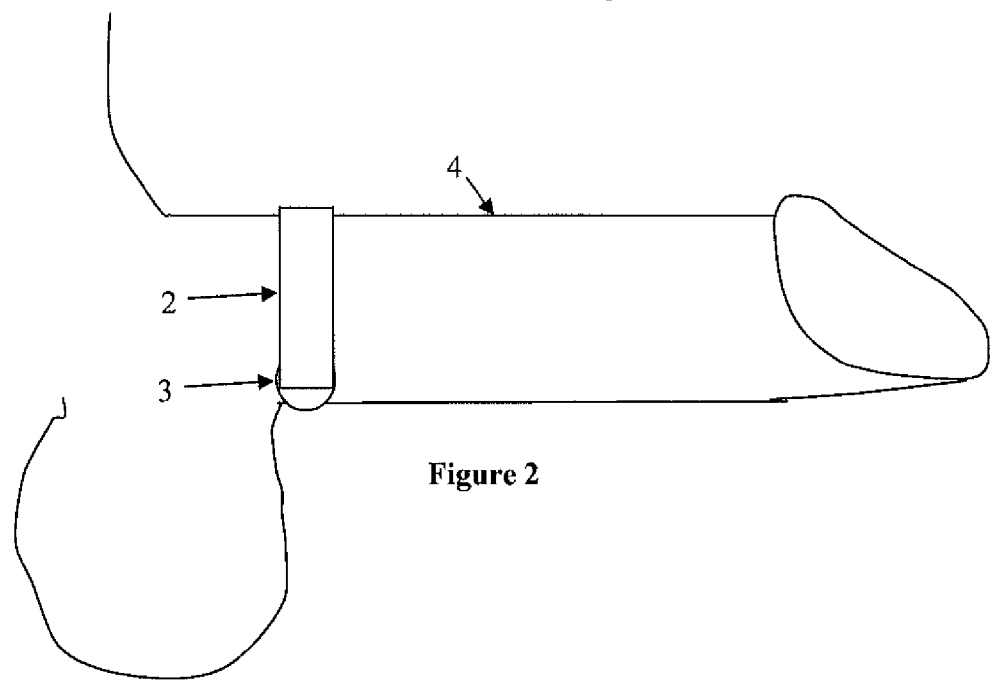
FIG. 2 shows a human penile organ wearing the male genital device

The device 1, as in shown in FIG. 2, has a substantially C-shape and is located partially around the penis near the pubic bone area. Magnets 3 attached to the distal end are in close contact with the penis' 4 skin. The two magnetic components placed at the main body distal ends are aligned in such way that they face each other with different polarization. The magnetic flux travels between each magnetic component 3 and around the main body 2, more particularly if the main body 2 is made of an antibacterial magnetic material.

Figure 3:
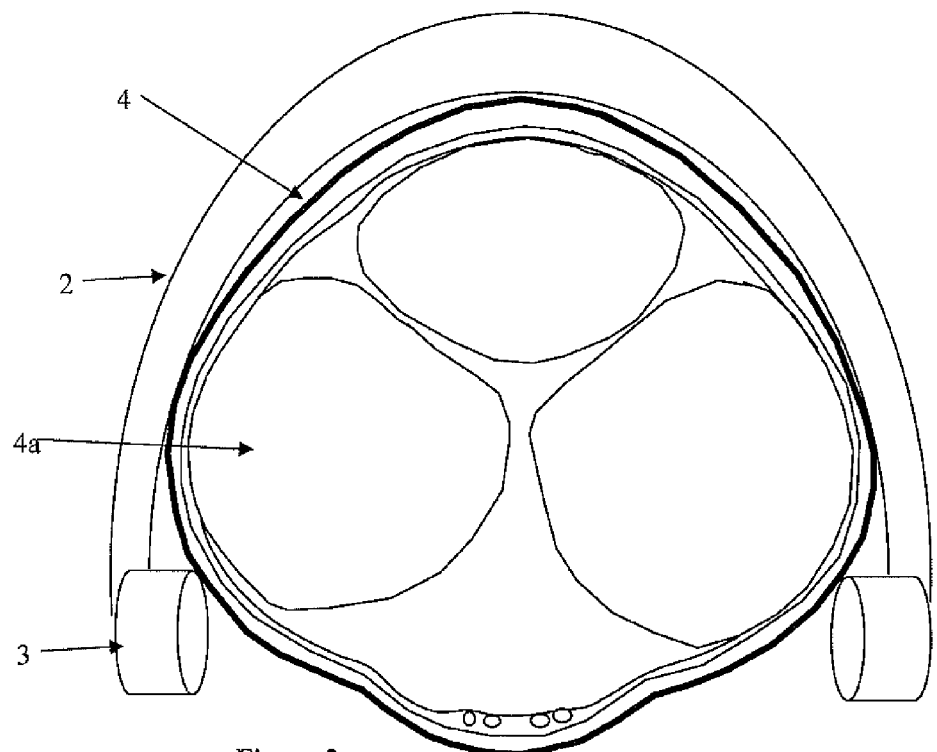
FIG. 3 is a cross-sectional view anatomy of a human penile organ wearing the male genital device.
Figure 4:
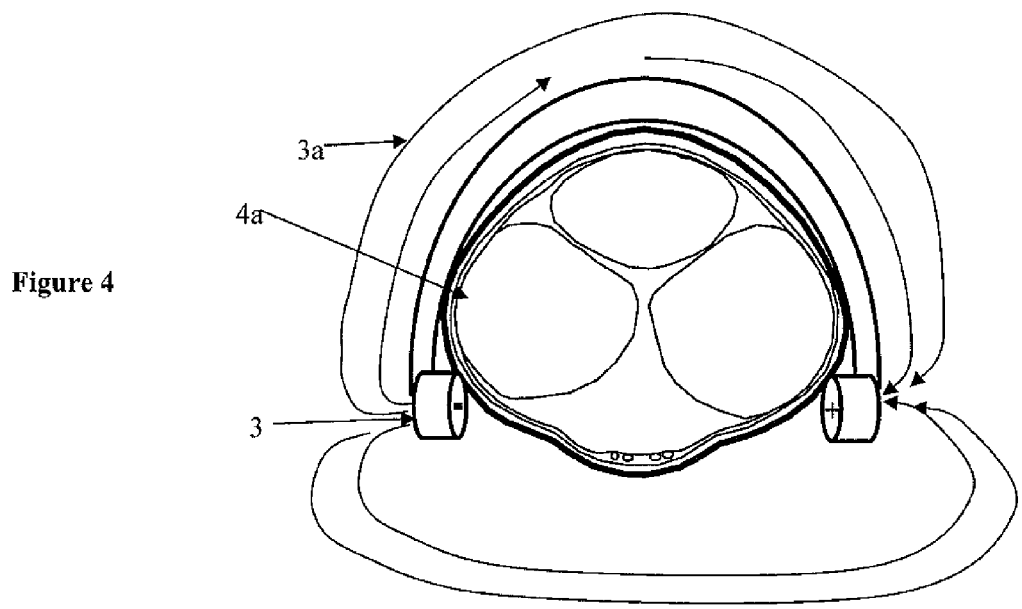
FIG. 4 shows the magnetic flux at work around the human penile organ.

The device 1 wraps around the male organ in such way that each magnetic component is substantially in close contact with the corpus cavernosum which are a pair of sponge-like regions of erectile tissue containing most of the blood during the male penis erection. FIG. 3 shows a cross section of the penis wherein the device 1 is in contact with the penis' 4 skins near the corpus cavernosum 4a. The magnetic flux 3a will travel around the penis surface as shown in FIG. 4. One of the advantages of using a flexible material is that the user manages to provide a curved shape that better fulfills his need.

Figure 5A:
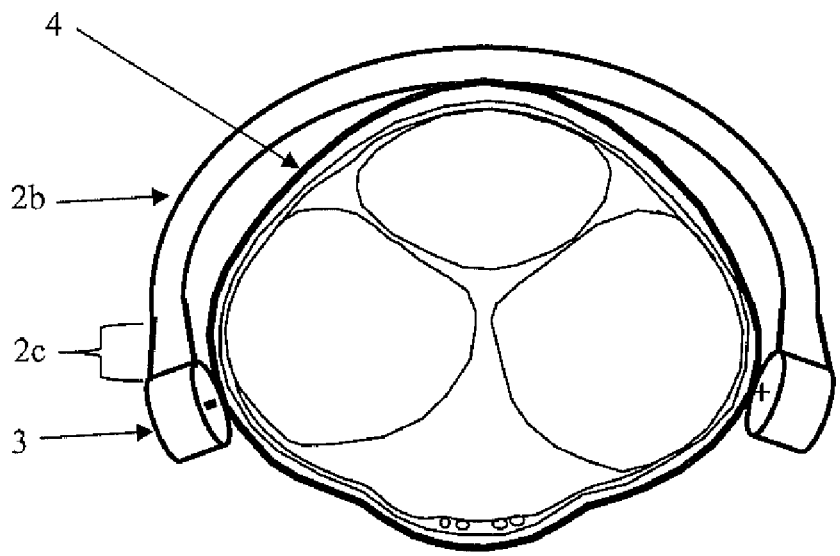
FIG. 5a-5b shows the male genital device with adjustable portion.
Figure 5B:
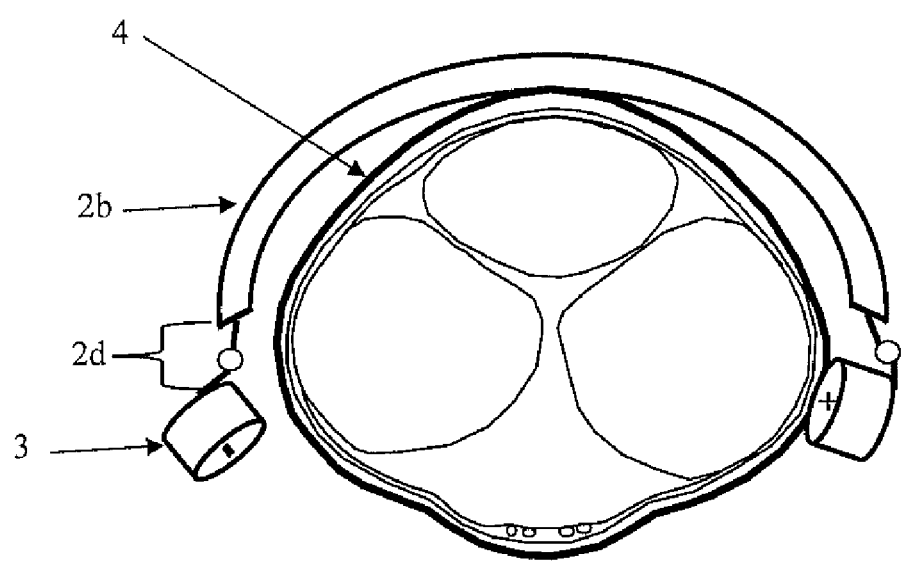

Even when a flexible material is used, the main body 2 can be separated in two portions as shown in FIGS. 5a and 5b, wherein the first portion is the substantially main center body 2b and the second portion is the distal end 2c. The main center body 2b can be made of a different material less flexible than the distal end in close contact with the magnets 3. The distal end 2b serves as a bridge between the main center body 2b and the magnets 3 while assisting the arrangement of the magnet 3 in such way that better contact is achieved with the skin near the corpus cavernosum providing an enhanced interaction between the magnetic field 3a and the penis 4. Another advantage of providing a more flexible area around the magnet 3 is that an easier assembling of the ring 1 is accomplished without jeopardizing or avoiding aesthetic changes on the ring's 1 main center body which is affected as a result of the bending. It has to be understood that in the instant case different materials with different flexibility properties are used however, for example in FIG. 5b, any other mechanism such as a resilient mechanism 2d comprising a spring can be used in order to provide an easier assembling avoiding aesthetic changes of the ring 1.

While the invention has been described as having a first design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

The invention claimed is:

1. A magnetic therapeutic device, comprising:
a main body and at least two magnetic components, wherein said main body comprises a substantially curved main center body and two distal ends;
wherein said main body is made of a flexible and adjustable material;
wherein said magnetic components are fixed to the distal ends of said main body;
wherein said distal ends serve as a bridge connecting the main center body and magnets, wherein said main center body and said distal ends are made of different materials; and
wherein said distal end material's flexibility is higher than said center body material's flexibility.

2. A magnetic therapeutic device, comprising:
a main body and at least two magnetic components, wherein said main body comprises a substantially curved main center body and two distal ends;
wherein said main body is made of a flexible and adjustable material;
wherein said magnetic components are fixed to the distal ends of said main body;
wherein said distal ends serves as a bridge connecting the main center body and magnets, wherein said main center body and said distal ends are made with different flexibility properties; and
wherein said distal ends comprises a resilient mechanism.

* * * * *